US011723992B2

(12) United States Patent
Lin et al.

(10) Patent No.: US 11,723,992 B2
(45) Date of Patent: Aug. 15, 2023

(54) METHOD FOR EXTRACTION AND PURIFICATION OF 68GA

(71) Applicant: Board of Regents, The University of Texas System, Austin, TX (US)

(72) Inventors: Mai Lin, Houston, TX (US); Carlos E. Gonzalez-Lepera, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/265,138

(22) PCT Filed: Aug. 2, 2019

(86) PCT No.: PCT/US2019/044938
§ 371 (c)(1),
(2) Date: Feb. 1, 2021

(87) PCT Pub. No.: WO2020/028825
PCT Pub. Date: Feb. 6, 2020

(65) Prior Publication Data
US 2021/0308287 A1    Oct. 7, 2021

Related U.S. Application Data

(60) Provisional application No. 62/714,190, filed on Aug. 3, 2018.

(51) Int. Cl.
| | | |
|---|---|---|
| *A61K 51/04* | (2006.01) | |
| *B01J 41/12* | (2017.01) | |
| *B01J 47/02* | (2017.01) | |
| *C01G 15/00* | (2006.01) | |
| *G21G 1/00* | (2006.01) | |
| *A61K 51/08* | (2006.01) | |
| *G21G 1/10* | (2006.01) | |

(52) U.S. Cl.
CPC ........ *A61K 51/088* (2013.01); *A61K 51/0402* (2013.01); *A61K 51/048* (2013.01); *A61K 51/0482* (2013.01); *A61K 51/08* (2013.01); *A61K 51/082* (2013.01); *A61K 51/083* (2013.01); *B01J 41/12* (2013.01); *B01J 47/02* (2013.01); *C01G 15/003* (2013.01); *G21G 1/001* (2013.01); *G21G 1/10* (2013.01); *C01P 2006/88* (2013.01); *G21G 2001/0021* (2013.01)

(58) Field of Classification Search
CPC .. A61K 51/00; A61K 51/0497; A61K 51/083; A61K 51/082; A61K 51/08; A61K 51/0482; A61K 51/048; A61K 51/0402; A61K 51/088; B01J 47/02; B01J 41/12; C01G 15/003; G21G 2001/0021; G21G 1/10; G21G 1/001; C01P 2006/88
USPC .............. 424/1.11, 1.37, 1.61, 1.65
See application file for complete search history.

(56) References Cited

U.S. PATENT DOCUMENTS

| | | | |
|---|---|---|---|
| 7,087,206 B2 | 8/2006 | Bond et al. | |
| 10,253,052 B2* | 4/2019 | Kung | A61P 19/00 |
| 2007/0031329 A1 | 2/2007 | Velikyan et al. | |
| 2013/0055855 A1 | 3/2013 | Le | |
| 2017/0029287 A1 | 2/2017 | Langstrom et al. | |
| 2018/0158559 A1* | 6/2018 | Abbasi | A61K 51/08 |

FOREIGN PATENT DOCUMENTS

| | | |
|---|---|---|
| WO | WO 2011/033120 | 3/2011 |
| WO | WO 2015/175972 | 11/2015 |
| WO | WO 2016/197084 | 12/2016 |

OTHER PUBLICATIONS

Alves et al., "Production of copper-64 and gallium-68 with a medical cyclotron using liquid targets," *Mod. Phys. Lett. A*, 32(17):1740013, 2017.
Ambrosini and Fanti, "68Ga-DOTA-peptides in the diagnosis of NET," *PET Clin.*, 9:37-42, 2014.
Amor-Coarasa et al., "Comprehensive quality control of the ITG 68Ge/68Ga generator and synthesis of 68Ga-DOTATOC and 68Ga-PSMA-HBED-CC for clinical imaging," *J. Nucl. Med.*, 57:1402-1405, 2016.
Belosi et al., "Generator breakthrough and radionuclidic purification in automated synthesis of 68Ga-DOTANOC," *Curr. Radiopharm*, 6:72-77, 2013.
Engle et al., "Very high specific activity $^{66/68}$Ga from zinc targets for PET," *Applied Radiation and Isotopes*, 70:1792-1796, 2012.
Jensen and Clark, "Direct production of Ga-68 from proton bombardment of concentrated aqueous solutions of [Zn-68] zinc chloride," In: Proceedings of the 13th International Workshop on Targetry and Target Chemistry Proceedings, pp. 288-292, 2011.
Larenkov et al., "Preparation of high-purity $^{68}$Ga solutions by ion exchange in mixed acetone-hydrochloric acid medium," *Radiochemistry*, 56(1):57-65, 2014.
Lin et al., "Production of curie quantities of $^{68}$Ga with a medical cyclotron via the $^{68}$Zn (p,n)$^{68}$Ga reaction," *Applied Radiation and Isotopes*, 133:1-3, 2018.
Lin et al., "Production of curie quantities of $^{68}$Ga with a medical cyclotron via the $^{68}$Zn (p,n)$^{68}$Ga reaction," *J Nucl Med*, 58(Suppl 1):Abstract 338, 2017.
Lindenberg et al., "Prostate cancer imaging with novel PET tracers," *Curr. Urol. Rep.*, 17:18, 2016.
McAlister et al., "Automated two col. generator systems for medical radionuclides," *Applied Radiation and Isotopes*, 67:1985-1991, 2009.
Moreira, "Cyclotron production of $^{68}$Ga using a $^{68}$Zn-based liquid target," Dissertation, University of Coimbra, 2013.

(Continued)

*Primary Examiner* — D. L. Jones
(74) *Attorney, Agent, or Firm* — Parker Highlander PLLC

(57) ABSTRACT

Disclosed herein are methods preparing a purified, carrier-free 68Ga solution. Tire present disclosure also provides systems for preparing a purified, carrier-free 68Ga solution. The present disclosure also provides compositions comprising the purified, carrier-free 68Ga solutions disclosed herein. Also provided are methods of administering compositions of the present disclosure to a patient in need thereof, for example, for imaging a disease or disorder, such as cancer.

15 Claims, 12 Drawing Sheets

(56) References Cited

OTHER PUBLICATIONS

Mueller et al., "Radiolabeling of DOTA-like conjugated peptides with generator-produced $^{68}$Ga and using NaCl-based cationic elution method," *Nat Protoc.*, 11(6):1057-1066, 2016.

Mueller et al., "Simplified NaCl based $^{68}$Ga concentration and labeling procedure for rapid synthesis of $^{68}$Ga radiopharmaceuticals in high radiochemical purity," *Bioconjugate Chemistry*, 23(8):1712-1717, 2012.

Pandey et al., "Cyclotron production of $^{68}$Ga via the $^{68}$Zn(p,n)$^{68}$Ga reaction in aqueous solution," *American Journal of Nuclear Medicine and Molecular Imaging*, 4(4):303-310, 2014.

PCT International Preliminary Report on Patentability issued in International Application No. PCT/US2019/044938, dated Feb. 18, 2021.

PCT International Search Report and Written Opinion issued in International Application No. PCT/US2019/044938, dated Dec. 6, 2019.

Prata, "Gallium-68: a new trend in PET radiopharmacy," *Curr. Radiopharm.*, 5:142-149, 2012.

Sadeghi et al. "Cyclotron production of $^{68}$Ga via proton-induced reaction on $^{68}$Zn target," *Nukleonika*, 54(1):25-28, 2009.

Schwenck et al., "Comparison of 68Ga-labelled PSMA-11 and 11C-choline in the detection of prostate cancer metastases by PET/CT," *Eur. J. Nucl. Med. Mol. Imaging*, 44:92-101, 2017.

Shamim et al., "PET/Computed tomography in neuroendocrine tumor: value to patient management and survival outcomes," *PET Clin.*, 10:411-421, 2015.

Siikanen, "Cyclotron produced Ga-66/68 with thermal diffusion-assisted bulk separation and AG50W-X8/UTEVA purification," Radiometals 2013 in Sonoma Valley, 7, Jun. 13-16, 2013.

Szelecsényi et al., "Investigation of direct production of 68Ga with low energy multiparticle accelerator," *Radiochim. Acta*, 100:5-11, 2012.

Tolmachev and Lundqvist, "Rapid separation of gallium from zinc targets by thermal diffusion," *Appl. Radiat. Isot.*: Tech. Note, 47:297-299, 1996.

Velikyan, "68Ga-Based radiopharmaceuticals: production and application relationship," *Molecules*, 20:12913-12943, 2015.

Virgolini et al., "Current knowledge on the sensitivity of the (68)Ga-somatostatin receptor positron emission tomography and the SUVmax reference range for management of pancreatic neuroendocrine tumours," *Eur. J. Nucl. Med. Mol. Imaging*, 43:2072-2083, 2016.

Vis et al., "GMP-compliant 68Ga radiolabelling in a conventional small-scale radiopharmacy: a feasible approach for routine clinical use" EJNMMI Res., 5:27, 2015.

Zhernosekov et al., "Processing of generator-produced $^{68}$Ga for medical application," *J Nucl Med*, 48:1741-1748, 2007.

\* cited by examiner

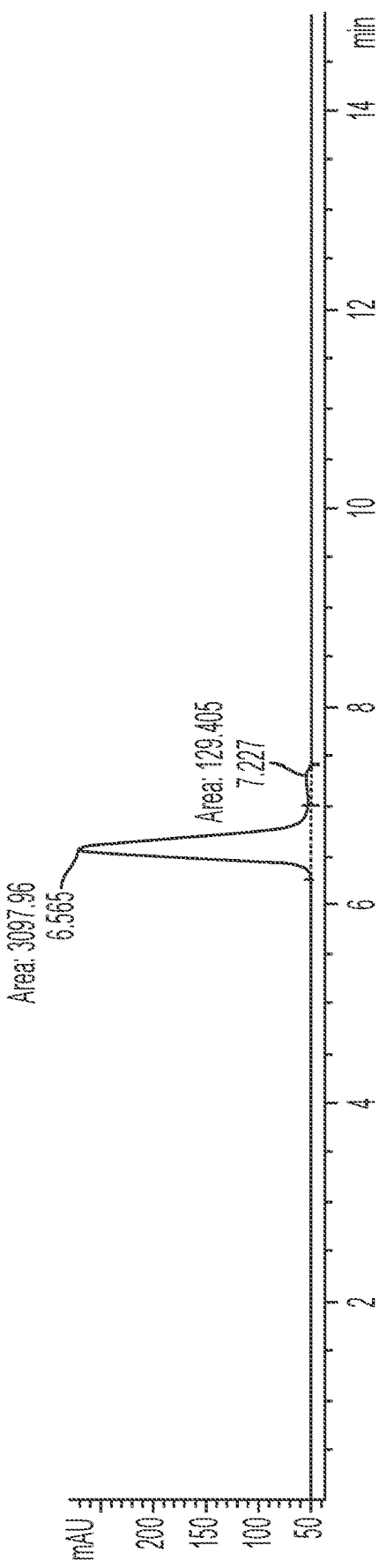
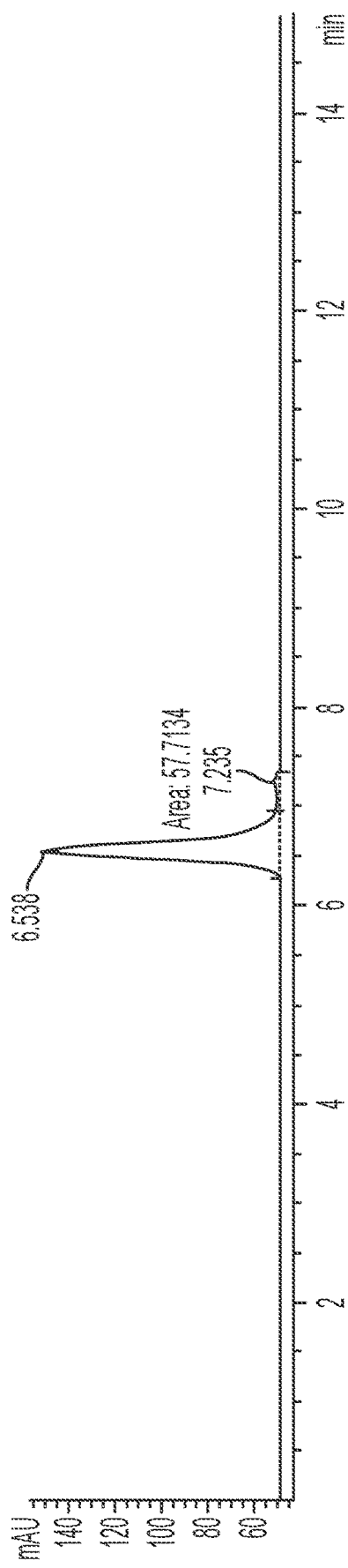
FIG. 3A
FIG. 3B

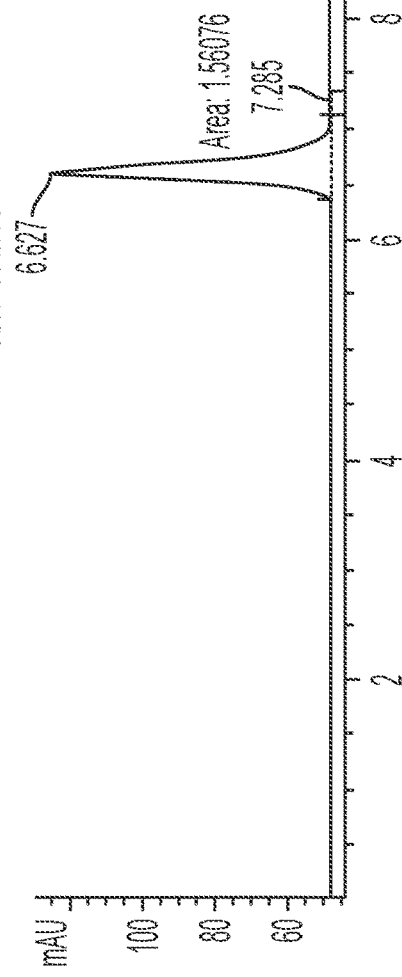
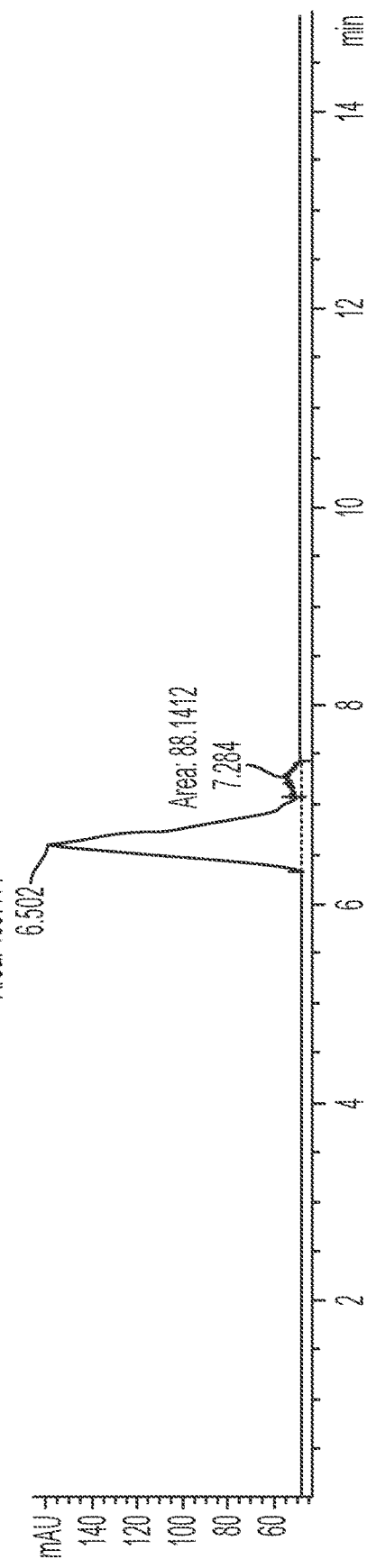
FIG. 7B
FIG. 7C

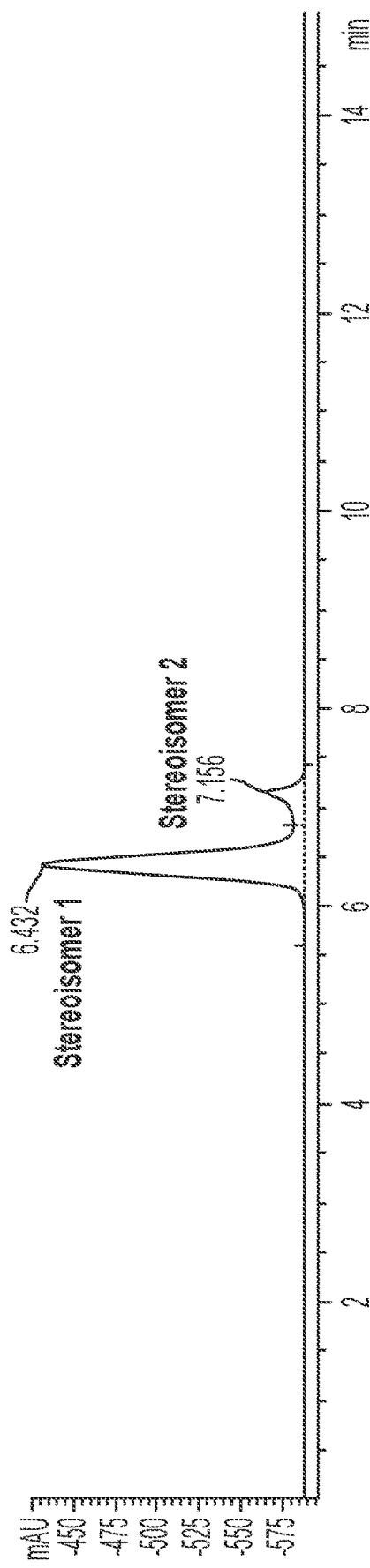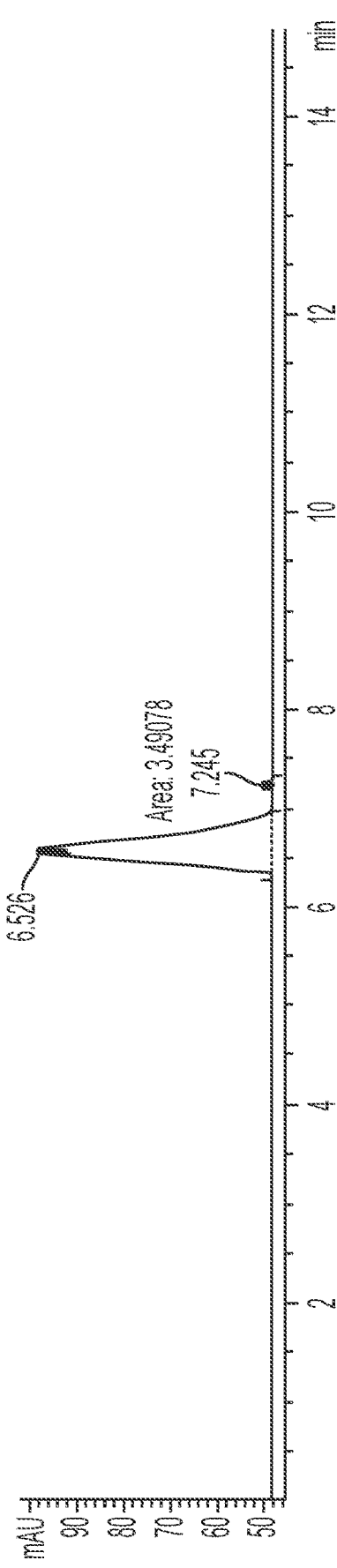

METHOD FOR EXTRACTION AND PURIFICATION OF 68GA

The present application is a national phase application under 35 U.S.C. § 371 of International Application No. PCT/US2019/044938, filed Aug. 2, 2019, which claims the priority benefit of U.S. provisional application No. 62/714,190, filed Aug. 3, 2018, the entire contents of each of which are incorporated herein by reference.

BACKGROUND

I. Field of the Invention

The present invention relates generally to the fields of chemistry and biological imaging. More particularly, it concerns methods for preparing purified $^{68}$Ga, systems for preparing purified $^{68}$Ga, compositions comprising purified $^{68}$Ga. and methods of use thereof.

II. Description of Related Art

The noticeable increase in PET imaging with $^{68}$Ga-labeled tracers over recent years has been marginally supported by the increased accessibility of $^{68}$Ge/$^{68}$Ga generators (Prata, 2012). Gallium-68 conveniently possesses two desirable properties, a short half-life (t1n: 68 min) and a high branching ratio for positron emission (β+%:89%). To date, $^{68}$Ga has been widely applied into various pre-clinical and clinical imaging studies. For instance, $^{68}$Ga-labeled somatostatin analogs have already demonstrated their value in imaging patients diagnosed with neuroendocrine tumors (Ambrosini and Fanti, 2014; Shamim et al., 2015; Virgolini et al., 2016). Recent reports indicate $^{68}$Ga-PSMA is superior to $^{11}$C/$^{18}$F-Choline in detecting more prostate cancer lesions, especially at lower prostate-specific antigen (PSA) levels in biochemically recurrent patients (Lindenberg et al., 2016; Schwenck et al., 2017). Given these results, the clinical promise of $^{68}$Ga-labeled radiopharmaceuticals clearly warrants the need to increase the availability of $^{68}$Ga for PET imaging applications.

Although current $^{68}$Ge/$^{68}$Ga generators can nominally deliver up to 1.85 GBq (50 mCi) of $^{68}$Ga per elution, nonetheless $^{68}$Ga activity decreases over time due to the decay of the parent nuclide $^{68}$Ge ($t_{1/2}$: 271 d). Furthermore, elution efficiencies around 80% of present activity are typical. In addition, the potential breakthrough of $^{68}$Ge with eluted $^{68}$Ga remains a concern (Belosi et al., 2013). Therefore, cyclotron production of $^{68}$Ga not only can provide an alternative way to meet the increasing demand for $^{68}$Ga, but also eliminates the possibility of $^{68}$Ge breakthrough.

Jensen and Clark reported the first attempt to produce $^{68}$Ga using a cyclotron with a liquid target filled with a $^{68}$ZnCl$_2$ solution (Jensen and Clark, 2011). Since then, Engle et al. have used a solid natZn target to produce $^{66/68}$Ga (Engle et al., 2012). The thermal diffusion method (Tolmachev and Lundqvist, 1996) to recover $^{66/68}$Ga from natural Zn foils presents advantages in processing time when thin (<0.1 mm) foils are considered (Siikanen, 2013). Pandey et al. tried to optimize $^{68}$Ga production through liquid targetry (Pandey et al., 2014). However, due to lengthy $^{68}$Ga separation steps reported by Engle et al. along with the relatively low production yields of $^{68}$Ga observed using liquid targetry, available $^{68}$Ga at end of processing is not significantly higher than generator produced isotope. Recently, medical cyclotron production of $^{68}$Ga from a Zn solid target has been shown to produce Curie quantities of $^{68}$Ga with low levels of $^6$Ge breakthrough.

Despite the improvement in methods to produce $^{68}$Ga, present methods for the purification of $^{68}$Ga produced by liquid or solid targetry require lengthy processing times due to the need for multiple purification steps. Due to the short half-life of $^{68}$Ga, there is a need for single-step purification protocols that can expediently deliver higher quantities of purified $^{68}$Ga for medical imaging applications.

SUMMARY OF THE INVENTION

The present disclosure provides methods for the purification of radionuclide solutions, including $^{68}$Ga solutions, and imaging agents prepared by these methods.

In some embodiments, the present disclosure provides methods of preparing a purified, carrier-free $^{68}$Ga solution comprising:

a) obtaining a $^{68}$Ga solution to be purified comprising $^{68}$Ga;

b) contacting the $^{68}$Ga solution with an anion-exchange resin; and c) eluting the $^{68}$Ga from the anion-exchange resin to obtain the purified, carrier-free $^{68}$Ga solution.

In some aspects, the method comprises contacting the $^{68}$Ga solution to be purified with a single anion-exchange resin. In some aspects, the method does not comprise contacting the $^{68}$Ga solution to be purified or the purified, carrier-free $^{68}$Ga solution with another ion-exchange resin. In some aspects, the $^{68}$Ga in the $^{68}$Ga solution to be purified is prepared by synthesizing the $^{68}$Ga in the $^{68}$Ga solution. In further aspects, a cyclotron is used to synthesize the $^{68}$Ga. In further aspects, the cyclotron comprises a metal sample in the form of a liquid target. In still further aspects, the metal sample comprises $^{68}$Zn$^{2+}$. In other aspects, the cyclotron comprises a metal sample in the form of a solid target. In further aspects, the metal sample comprises $^{68}$Zn. In some aspects, the $^{68}$Ga solution to be purified comprises an acid. In further aspects, the acid has a concentration of greater than about 2 N. In still further aspects, the acid has a concentration of from about 3 N to about 10 N, such as about 6 N. In some aspects, the acid is HCl or is derived from the dissociation of HCl. In some aspects, the $^{68}$Ga solution to be purified is an aqueous solution.

In some aspects, the anion-exchange resin comprises a phosphonate or a substituted phosphonate. In some aspects the anion-exchange resin comprises a phosphonate, such as dipentyl pentylphosphonate. In some aspects, the methods further comprise washing the anion-exchange resin with a washing solution. In some aspects, the washing step occurs before the eluting step.

In some aspects, the washing solution comprises an acid. In some aspects, the acid has a concentration of greater than about 1 N. In further aspects, the acid has a concentration of from about 2 N to about 8 N, such as about 4 N. In some aspects, the acid is HCl or is derived from the dissociation of HCl. In some aspects, the washing solution is an aqueous solution.

In some aspects, eluting comprises contacting the anion-exchange resin with an eluting solution. In some aspects, the eluting solution comprises as acid. In some aspects, the acid has a concentration of from about 0.005 N to about 2 N. In further aspects, the acid has a concentration from about 0.01 N to about 1 N, such as about 0.05 N. In some aspects, the acid is HCl or is derived from the dissociation of HCL. In some aspects, the eluting solution is an aqueous solution.

In some aspects, the purified, carrier-free $^{68}$Ga solution has an activity of from about 37 MBq to about 370 GBq. In further aspects, the purified, carrier-free $^{68}$Ga solution has an activity of from about 370 MBq to about 370 GBq. In still further aspects, the purified, carrier-free $^{68}$Ga solution has an activity of from about 3.7 GBq to about 370 GBq. In some aspects, the purified, carrier-free $^{68}$Ga solution comprises less than about 1 µg/GBq of zinc. In further aspects, the purified, carrier-free $^{68}$Ga solution comprises less than about 0.1 µg/GBq of zinc. In still further aspects, the purified, carrier-free $^{68}$Ga solution comprises less than about 0.01 µg/GBq of zinc. In some aspects, the purified, carrier-free $^{68}$Ga solution comprises less than about 10 µg/GBq of iron. In further aspects, the purified, carrier-free $^{68}$Ga solution comprises less than about 1 µg/GBq of iron. In still further aspects, the purified, carrier-free $^{68}$Ga solution comprises less than about 0.5 µg/GBq of iron. In some aspects, the purified, carrier-free $^{68}$Ga solution comprises less than about 1 µg/GBq of germanium. In further aspects, the purified, carrier-free $^{68}$Ga solution comprises less than about 0.01 µg/GBq of germanium. In still further aspects, the purified, carrier-free $^{68}$Ga solution comprises less than about 0.0001 µg/GBq of germanium.

In some aspects, the purified, carrier-free $^{68}$Ga solution has a specific activity of greater than about 25 GBq/µg. In further aspects, the purified, carrier-free $^{68}$Ga solution has a specific activity of from about 25 GBq/µg to about 100.000 GBq/µg. In further aspects, the purified, carrier-free (Ga solution has a specific activity of from about 100 GBq/µg to about 100,000 GBq/µg. In further aspects, the purified, carrier-fee $^{68}$Ga solution has a specific activity of from about 1,000 GBq/µg to about 100,000 GBq/µg. In further aspects, the purified, carrier-free $^{68}$Ga solution has a specific activity of from about 10,000 GBq/µg to about 80,000 GBq/µg. In further aspects, the purified, carrier-free $^{68}$Ga solution has a specific activity of from about 25,000 GBq/µg to about 50,000 GBq/µg. In still further aspects, the purified, carrier-free $^{68}$Ga solution has a specific activity of from about 31,000 GBq/µg to about 36,000 GBq/µg. In some embodiments, the present disclosure provides purified, carrier-free $^{68}$Ga solutions prepared according to methods disclosed herein.

In some embodiments, the present disclosure provides systems for preparing a purified, carrier-free $^{68}$Ga solution comprising:

a) a solid target comprising $^{68}$Zn;

b) a cyclotron, wherein the solid target is irradiated using the cyclotron; and c) an anion-exchange resin.

In some aspects, the system comprises a single anion-exchange resin. In some aspects, the system does not comprise another ion-exchange resin. In some aspects, the anion-exchange resin comprises a phosphonate or a substituted phosphonate. In some aspects, the anion-exchange resin comprises a phosphonate, such as dipentyl pentylphosphonate. In some aspects, the purified, carrier-free $^{68}$Ga solution has a specific activity of from about 25 GBq/µg to about 100,000 GBq/µg. In further aspects, the purified, carrier-free $^{68}$Ga solution has a specific activity of from about 100 GBq/µg to about 100.000 GBq/µg. In further aspects, the purified, carrier-free $^{68}$Ga solution has a specific activity of from about 1,000 GBq/µg to about 100,000 GBq/µg. In further aspects, the purified, carrier-free $^{68}$Ga solution has a specific activity of from about 10,000 GBq/µg to about 85,000 GBq/µg. In further aspects, the purified, carrier-free $^{68}$Ga solution has a specific activity of from about 25,000 GBq/µg to about 50,000 GBq/µg. In still further aspects, the purified, carrier-free $^{68}$Ga solution has a specific activity of from about 31,000 GBq/µg to about 36,000 GBq/µg.

In some embodiments, the present disclosure provides compositions comprising the purified, carrier-free $^{68}$Ga solutions disclosed herein. In some aspects, the compositions further comprise a carrier molecule, wherein the carrier molecule is radiolabeled with the $^{68}$Ga of the purified, carrier-free $^{68}$Ga solution. In further aspects, the carrier molecule is an antibody or a fragment thereof. In other aspects, the carrier molecule is a peptide or a fragment thereof. In other aspects, the carrier molecule is prostate-specific membrane antigen (PSMA), 1,4,7-triazacyclononane-N,N',N"-triacetic acid (NOTA), 1,4,7,10-tetraazacyclododecane-1,4,7,10-tetraacetic acid (DOTA), diethylene triamine pentaacetic acid (DTPA), desferrioxamine, DOTA-Tyr(3)-octreotide (DOTATOC), DOTA-Tyr(3)-Tyr(8)-octreotide (DOTATATE), DOTA-1-naphtyl-alanine (DOTANOC), DOTA-benzothienyl-alanine (DOTA-BOC), DOTA-bombesin, DOTA-arginine-glycine-aspartic acid-bombesin (DOTA-RGD-bombesin), NOTA-RGD, 3,6,9,15-tetraazabicyclo[9.3.1]pentadeca-1(15)-,11,13-triene-3,6,9-triacetic acid-RGD (PCTA-RGD), DOTA-albumin, DOTA-human epidermal growth factor, 1,4,7-triazacyclononane-1-[methyl(2-carboxyethyl)phosphinic acid]-4,7-bis[methyl(2-hydroxymethyl)phosphinic acid-integrin alpha(IIb)beta(3)-specific cyclic hexapeptide (NOPO-RGDfK), 1,4,7-triazacyclononane-1,4-bis(acetic acid)-7-(2-glutaric acid) (NODAGA). NOPO—NaI(3)-octreotide conjugate (NOPO—NOC), 1,4,7-triazacyclononane-1,4,7-tris[(2-carboxyethyl)methylenephosphonic acid] (TRAP(RGD)$_3$), or citrate. In further aspects, the carrier molecule is PSMA, DOTATATE, DOTATOC, DOTANOC, or citrate. In some aspects, the carrier molecule is PSMA. In other aspects, the carrier molecule is DOTATATE. In still other aspects, the carrier molecule is citrate. In some aspects, the carrier molecule targets a human tissue. In some aspects, the human tissue is selected from the following: thyroid, brain, gastrointestinal, pancreas, spleen, kidney, neuroendocrine tumors, renal cell carcinoma, lung cancer, breast cancer, prostate cancer, and malignant lymphoma.

In some embodiments, the present disclosure provides methods of imaging comprising administering a composition disclosed herein to a patient. In some aspects, the patient is a mammal. In further aspects, the mammal is a human. In some aspects, the composition is administered more than once. In other aspects, the composition is administered once. In some aspects, the composition is formulated for administration intraarterially, intraarticularly, intracranially, intrapericardially, intraperitoneally, intratumorally, intravenously, intravesicularlly, parenterally, via injection, via local delivery, or via localized perfusion. In some aspects, the composition is formulated for administration intravenously. In some aspects, the composition is formulated as a unit dose. In some aspects, the methods further comprise imaging a tumor. In some aspects, the tumor is a neuroendocrine tumor. In some aspects, the tumor expresses elevated levels of PSMA. In further aspects, the tumor is a pancreatic tumor, a prostate tumor, or a lung tumor. In some aspects, the tumor is a pancreatic tumor. In other aspects, the tumor is a prostate tumor. In still other aspects, the tumor is a lung tumor.

In other embodiments, the present disclosure provides methods of preparing a purified, carrier-free $^{68}$Ga solution having a specific activity of greater than about 25 GBq/µg comprising:

a) obtaining a $^{68}$Ga solution to be purified comprising $^{68}$Ga;

b) contacting the $^{68}$Ga solution with an ion-exchange resin; and c) eluting the $^{68}$Ga from the ion-exchange resin to obtain the purified, carrier-free $^{68}$Ga solution.

In some aspects, the method comprises a single ion-exchange resin. In some aspects, the method does not comprise another ion-exchange resin.

In still other embodiments, the present disclosure provides methods of preparing a purified, carrier-free $^{68}$Ga solution having a specific activity of greater than about 25 GBq/μg comprising:

a) obtaining a $^{68}$Ga solution to be purified comprising $^{68}$Ga;

b) contacting the $^{68}$Ga solution with an anion-exchange resin; and c) eluting the $^{68}$Ga from the anion-exchange resin to obtain the purified, carrier-free $^{68}$Ga solution.

In some aspects, the method comprises a single anion-exchange resin. In some aspects, the method does not comprise another ion-exchange resin.

In still other embodiments, the present disclosure provides systems for preparing a purified, carrier-free $^{68}$Ga solution having a specific activity of greater than about 25 GBq/μg comprising:

a) a solid target comprising $^{68}$Zn;

b) a cyclotron, wherein the solid target is irradiated using the cyclotron; and c) an ion-exchange resin.

In some aspects, the system comprises a single ion-exchange resin. In some aspects, the system does not comprise another ion-exchange resin.

In still other embodiments, the present disclosure provides systems for preparing a purified, carrier-free $^{68}$Ga solution having a specific activity of greater than about 25 GBq/μg comprising:

a) a solid target comprising $^{68}$Zn;

b) a cyclotron, wherein the solid target is irradiated using the cyclotron; and c) a single anion-exchange resin.

In some aspects, the system comprises a single anion-exchange resin. In some aspects, the system does not comprise another ion-exchange resin.

Other objects, features, and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A shows labeling test with 100 μg of DOTA-Oct and 100 mCi of $^{68}$Ga (radiochemical yield=98.4%, radiochemical purity=94.2%). FIG. 1B shows labeling test with 50 μg of DOTA-Oct and 100 mCi of $^{68}$Ga (radiochemical yield=99.2%, radiochemical purity=96.7%). FIG. 1C shows labeling test with 25 μg of DOTA-Oct and 100 mCi of $^{68}$Ga (radiochemical yield=96.5%, radiochemical purity=88.1%).

FIG. 2A shows labeling test with 100 μg of PSMA-11 and 100 mCi of $^{68}$Ga (radiochemical yield=100%, radiochemical purity=>99%). FIG. 2B shows labeling test with 50 sg of PSMA-11 and 100 mCi of $^{68}$Ga (radiochemical yield=100%, radiochemical purity=>99%). FIG. 2C shows labeling test with 25 μg of PSMA-11 and 100 mCi of $^{68}$Ga (radiochemical yield=100%, radiochemical purity=>99%).

FIGS. 3A-3C show HPLC traces of PSMA-11 labeling tests with cyclotron-produced $^{68}$Ga (conditions: pH 4, 95° C. for 10 minutes). FIG. 3A shows labeling test with 10 μg of PSMA-11 and 100 mCi of $^{68}$Ga (radiochemical yield=100%, radiochemical purity=>99%). FIG. 3B shows labeling test with 5 μg of PSMA-11 and 100 mCi of $^{68}$Ga (radiochemical yield=100%, radiochemical purity=>99%). FIG. 3C shows labeling test with 1 μg of PSMA-11 and 100 mCi of $^{68}$Ga (radiochemical yield=74%, radiochemical purity=38.1%).

FIG. 4A shows radiochemical yield=87.4% and radiochemical purity=62.9% at 0 h; FIG. 4B shows radiochemical purity=17% at 3 h.

FIG. 5A shows labeling test at 0 h: radiochemical yield=100%, radiochemical purity=>99%; FIG. 5B shows labeling test at 1 h: radiochemical purity=~66.6%; FIG. 5C shows labeling test at 3 h: radiochemical purity=~47.9%.

FIGS. 7A-7C show HPLC traces of PSMA-11 labeling tests with cyclotron-produced $^{68}$Ga (conditions: 0.5 Ci $^{68}$Ga, 125 μg PSMA-11, 200 mg L-ascorbic acid, pH 4, 95° C. for 10 minutes) after 0 h (radiochemical purity=>99%. FIG. 7A), 1 h (radiochemical purity=>99%, FIG. 7B), and 4 h (radiochemical purity=>99%, FIG. 7C).

FIGS. 8A & 8B show HPLC traces of PSMA-11 labeling tests with generator-produced 10 $^{68}$Ga. FIG. 8A shows the HPLC trace of a standard of $^{68}$Ga-PSMA-11. FIG. 8B shows the HPLC trace of PSMA-11 with generator-produced $^{68}$Ga (conditions: 0.5 18 mCi $^{68}$Ga, 50 μg PSMA-11, pH 4, 95° C. for 10 minutes) and shows radiochemical yield=100% and radiochemical purity=>99%.

DESCRIPTION OF ILLUSTRATIVE EMBODIMENTS

I. Introduction

Figure 1A:
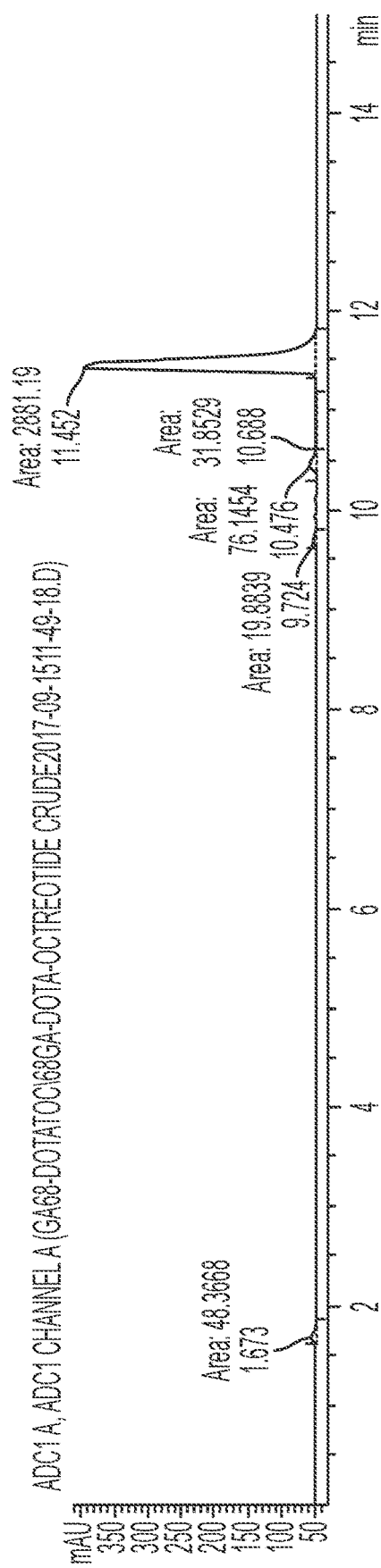
FIGS. 1A-1C show HPLC traces of DOTA-Oct labeling tests with cyclotron-produced $^{68}$Ga (conditions: pH 4.5, 95° C. for 10 minutes).
Figure 1B:
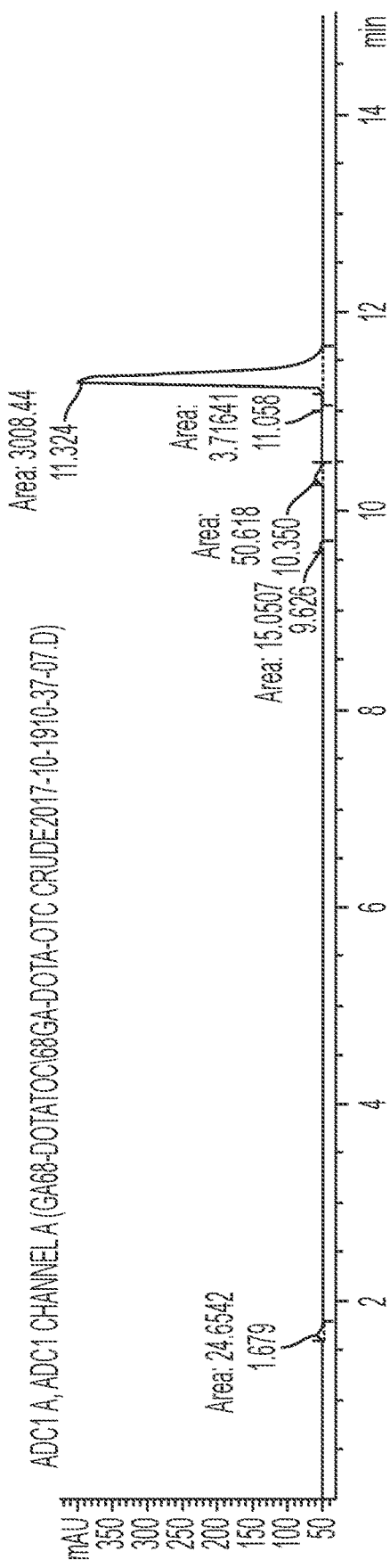
Figure 1C:
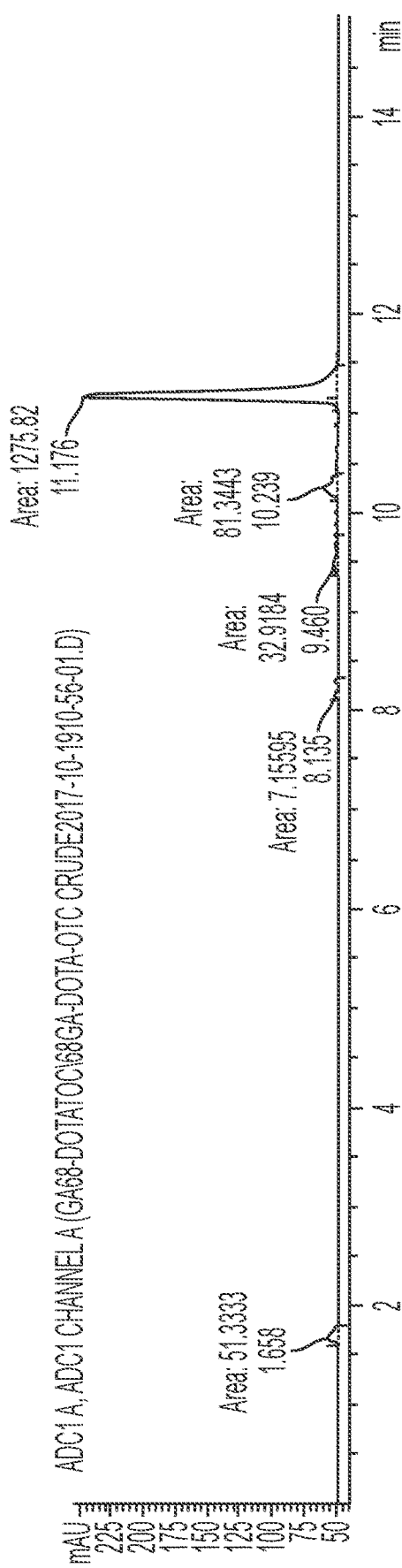
Figure 2A:
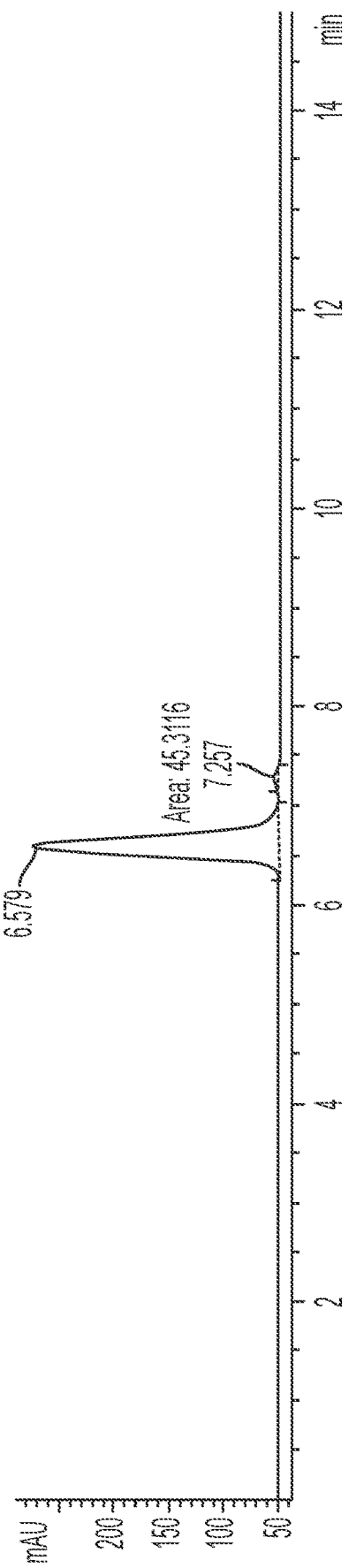
FIGS. 2A-2C show HPLC traces of PSMA-11 labeling tests with cyclotron-produced $^{68}$Ga (conditions: pH 4, 95° C. for 10 minutes).
Figure 2B:
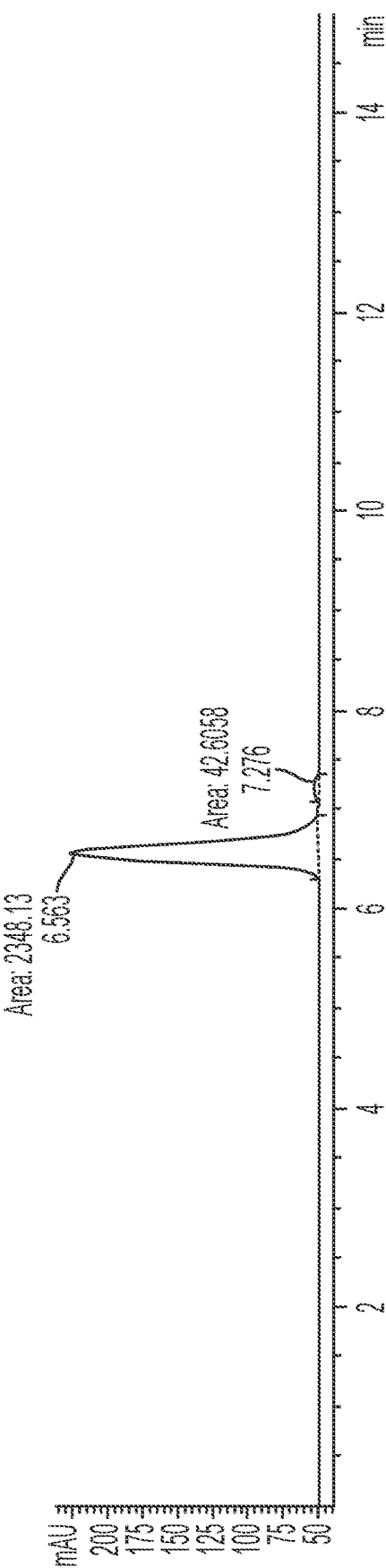
Figure 2C:
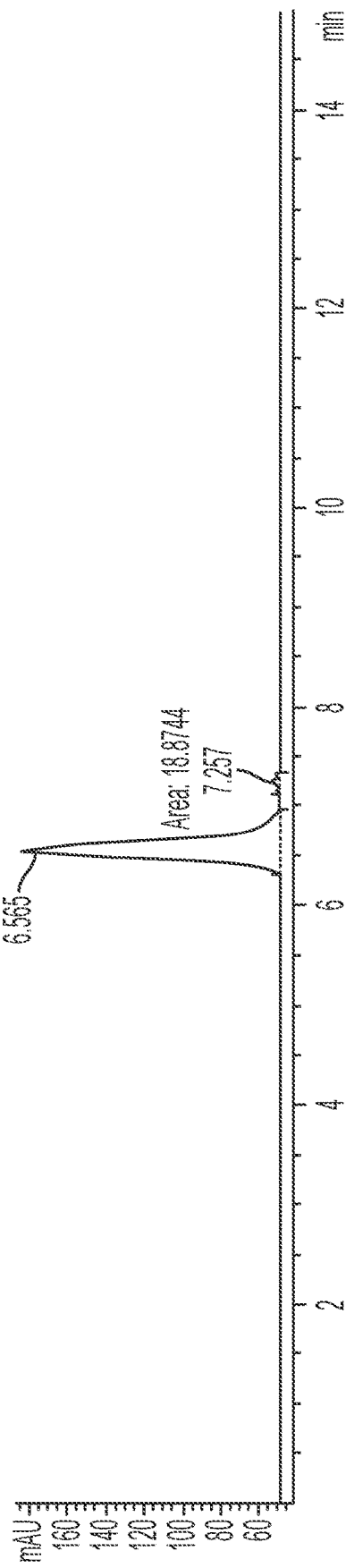
Figure 3C:
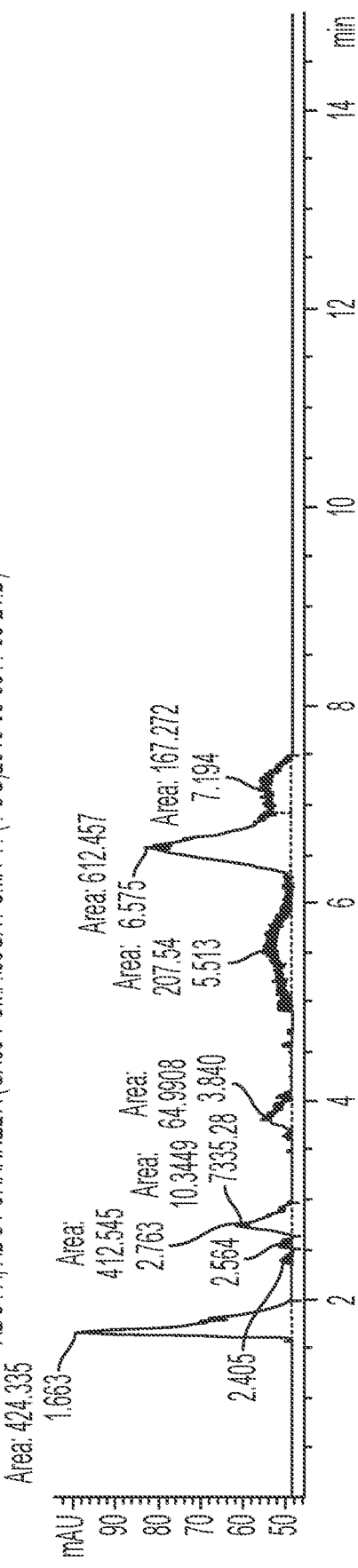
Figure 4A:
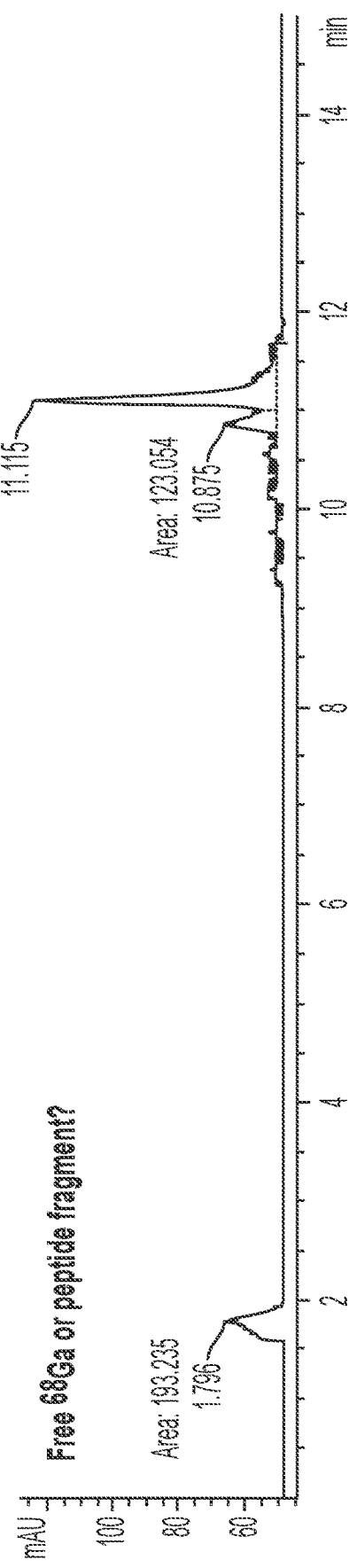
FIGS. 4A & 4B show HPLC traces of large-scale labeling tests with DOTA-Oct with cyclotron-produced $^{68}$Ga (conditions: 1 Ci $^{68}$Ga, 500 μg DOTA-Oct, pH 4, 95° C. for 10 minutes).
Figure 4B:
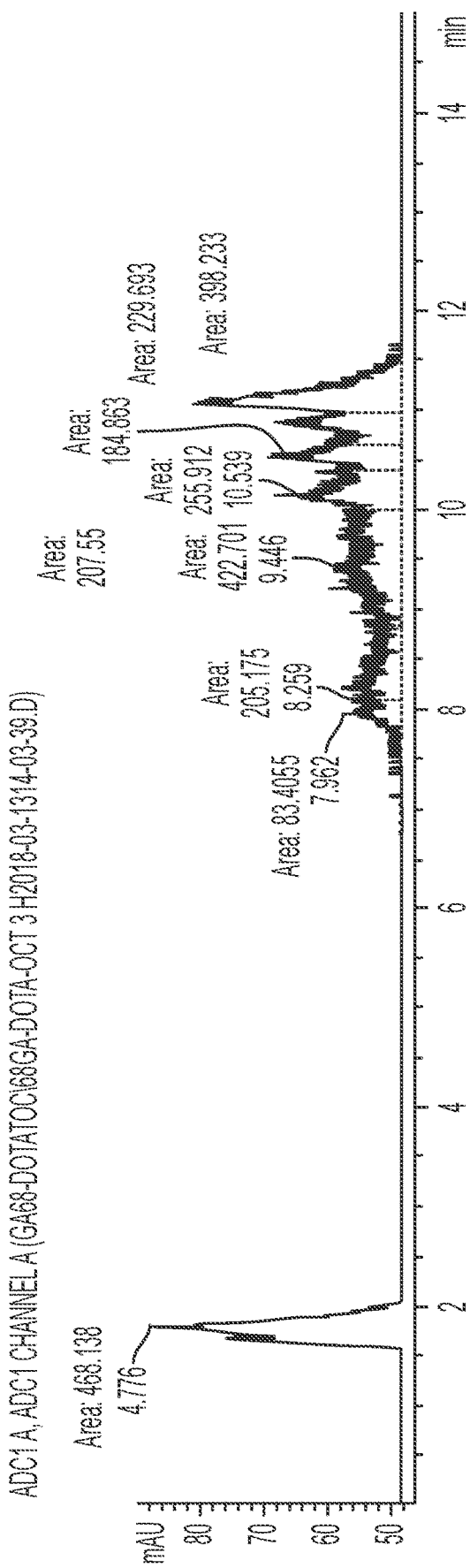
Figure 5A:
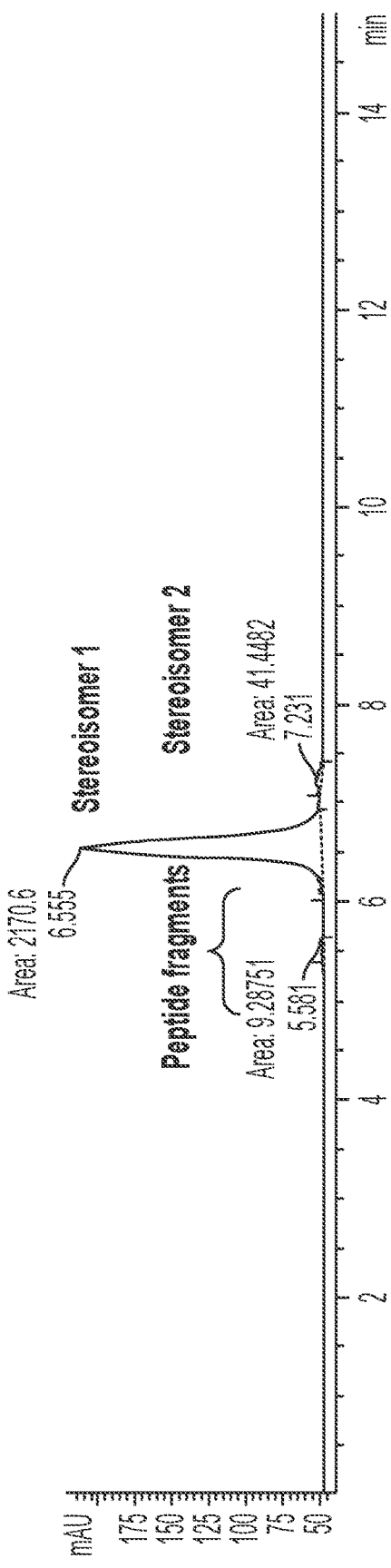
FIGS. 5A-5C show HPLC traces of large-scale labeling tests with PSMA-11 with cyclotron-produced $^{68}$Ga (conditions: 0.5 Ci $^{68}$Ga, 125 μg PSMA-11, pH 4, 95° C. for 10 minutes).
Figure 5B:
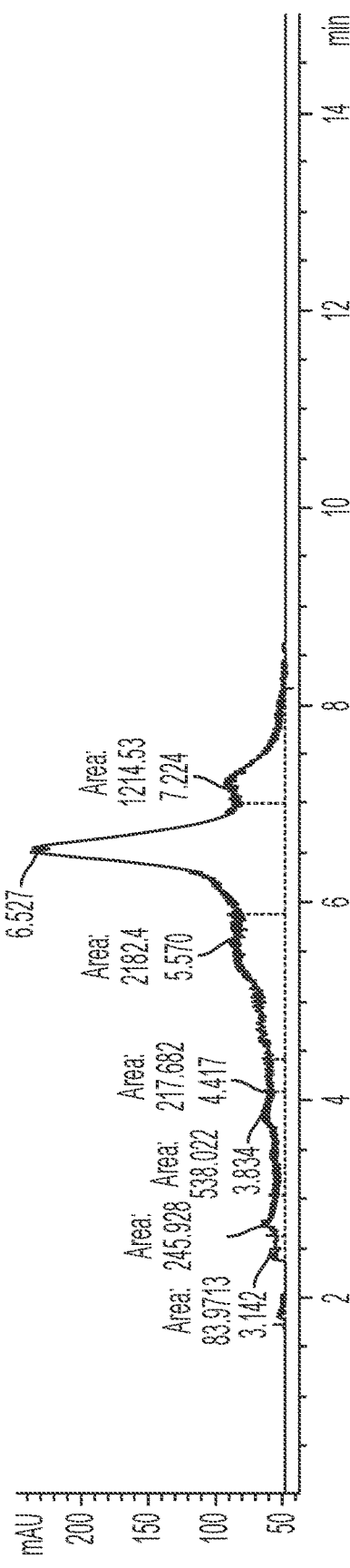
Figure 5C:
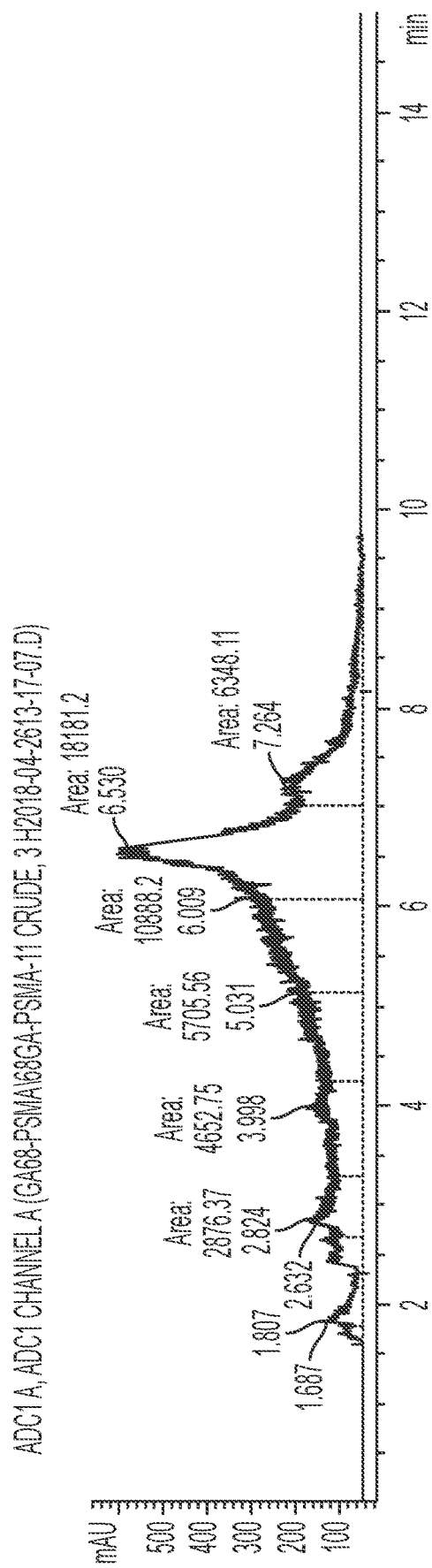
Figure 6A:
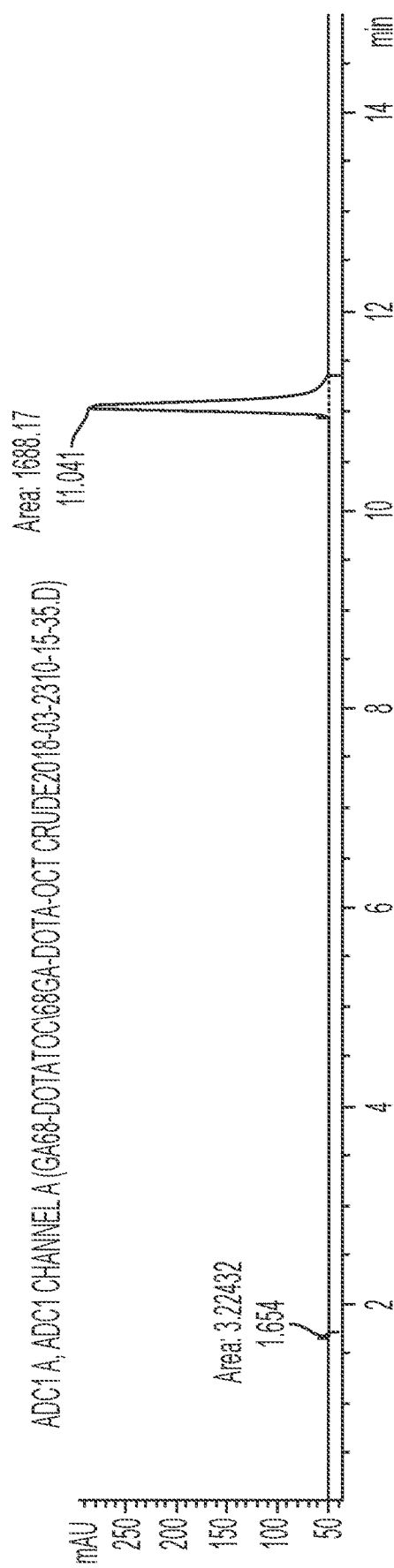
FIGS. 6A-6C show HPLC traces of DOTA-Oct labeling tests with cyclotron-produced $^{68}$Ga (conditions: 0.5 Ci $^{68}$Ga, 250 μg DOTA-Oct, 200 mg L-ascorbic acid, pH 4.5, 95° C. for 10 minutes) after 0 h (radiochemical purity=>99%, FIG. 6A), 1 h (radiochemical purity=>99%, FIG. 6B), and 4 h (radiochemical purity=>99%, FIG. 6C).
Figure 6B:
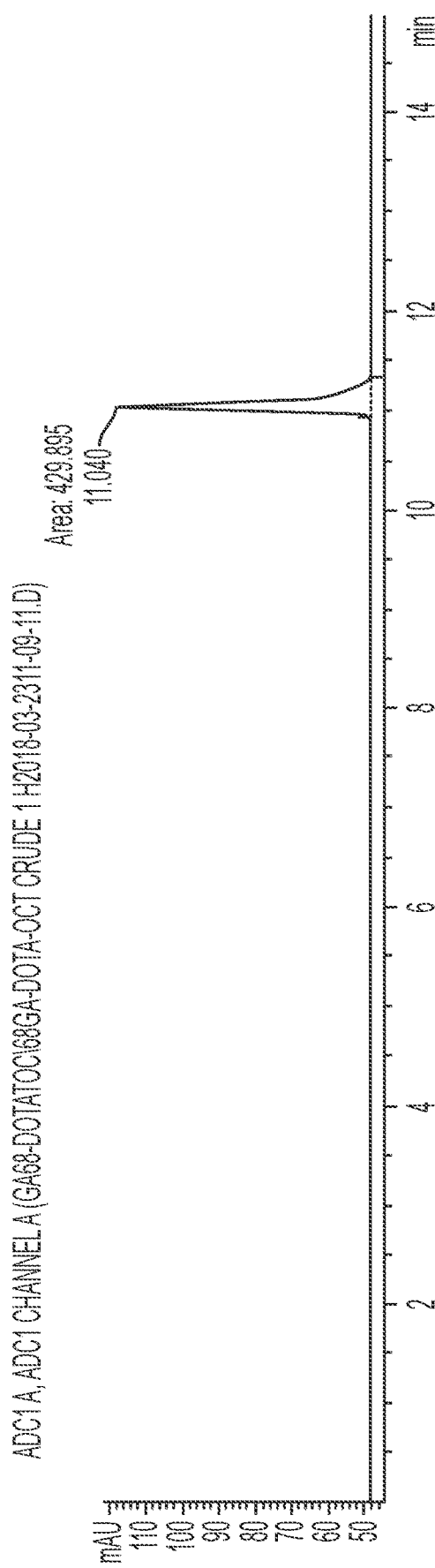
Figure 6C:
Figure 7A:
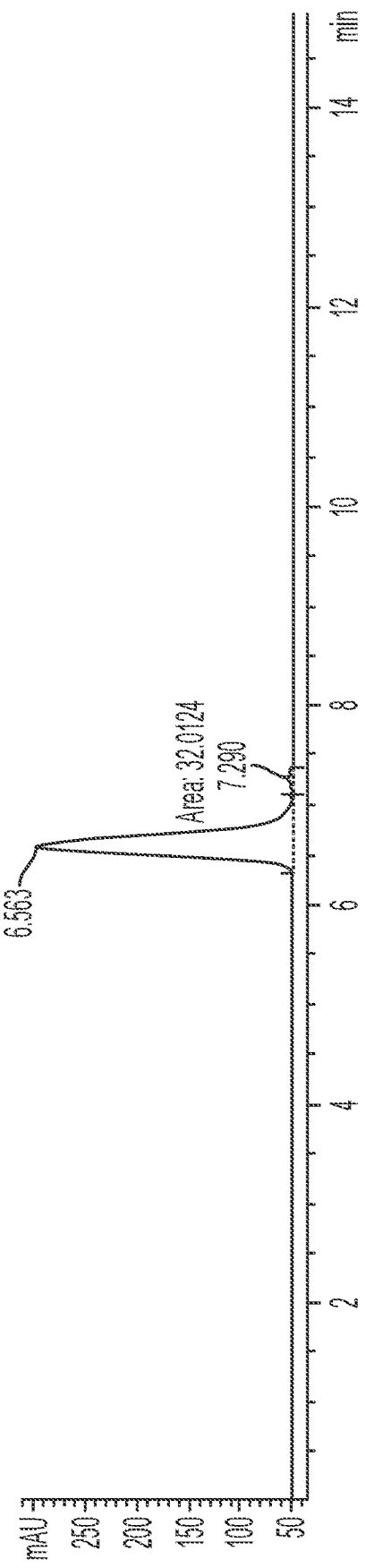

Disclosed herein are methods and systems for the rapid purification of $^{68}$Ga solutions, compositions comprising $^{68}$Ga solutions prepared using said methods and systems, as well as methods of using said compositions to image biological tissues, such as tumors. The methods of purification comprise contacting a solution of $^{68}$Ga to be purified with a single anion-exchange resin.

Gallium-68 is a positron-emitting radioisotope that can be produced from a $^{68}$Ge/$^{68}$Ga generator or from proton beam bombardment of $^{68}$Zn in a cyclotron. $^{68}$Ga-labeled peptides are a valuable class of radiopharmaceuticals exhibiting fast target localization and blood clearance. $^{68}$Ga-DOTATOC, $^{68}$Ga-DOTATATE, $^{68}$Ga-DOTANOC, are the most prominent radiopharmaceuticals currently in use for imaging and differentiating lesions of various somatostatin receptor subtypes, overexpressed in many neuroendocrine tumors. The number of clinical trials with $^{68}$Ga has increased dramatically, including within the United States.

As demand for $^{68}$Ga increases for use in radiopharmaceuticals, the need for improved methods for the synthesis and subsequent processing of $^{68}$Ga has grown significantly. Current methods for processing $^{68}$Ga require multiple purification steps (i.e. passing the crude $^{68}$Ga solution through more than one ion-exchange resin) and/or additional concentration and reconstitution steps in order to achieve a purity level and concentration sufficient to radiolabel carrier molecules for administration to patients. Such additional processing steps take time and leads to a lower specific activity of the purified $^{68}$Ga as a result of the short half-life of $^{68}$Ga (~68 minutes). As such, there is a need for methods that can produce purified $^{68}$Ga quickly while removing unwanted impurities such as zinc, iron, and/or germanium.

This invention is based, in part, on the discovery of a fully defined process of preparing purified $^{68}$Ga using a single anion-exchange resin which rapidly and directly provides the purified $^{68}$Ga in a solution sufficient such that no further processing is required prior to use in radiolabeling. As shown in the Examples, there is provided a method to prepare a purified, carrier-free solution of $^{68}$Ga with very high specific activity.

II. Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device employed to determine the value, the method being employed to determine the value, or the variation that exists among the study subjects or patients.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

Unless specified otherwise, any chemical group or compound class listed in a claim set has a carbon atom limit of less than or equal to twelve.

In the context of chemical formulas, the symbol "—" means a single bond, "=" means a double bond, and "≡" means triple bond. The symbol "- - - -" represents an optional bond, which if present is either single or double. The symbol ⇌ represents a single bond or a double bond. Thus, the formula

covers, for example

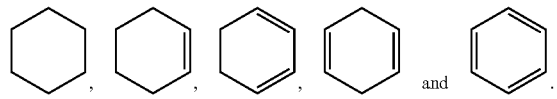

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol ∿∿, when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol ◤ means a single bond where the group attached to the thick end of the wedge is "out of the page." The symbol ⫽⫽⫽ means a single bond where the group attached to the thick end of the wedge is "into the page". The symbol ∿∿ means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

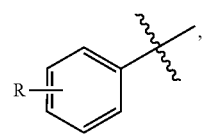

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

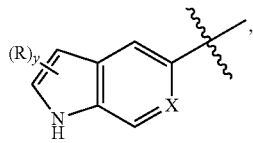

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$Cl (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$) CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C (CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C (O)OH, —CH$_2$C(O)OCH$_3$, —CH$_2$C(O)NH$_2$, —CH$_2$C(O) CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

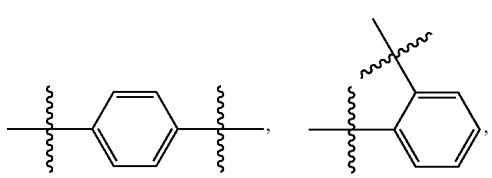

-continued

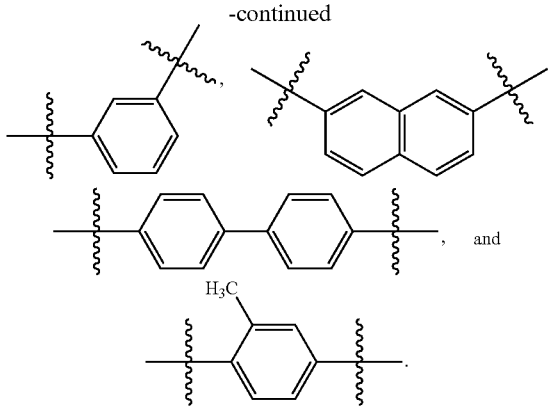

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "phosphonate" when used without the "substituted" modifier refers to a compound with the formula R—P(O)(OR')(OR"), in which R, R', and R" can be the same or different alkyl, aryl, or aralkyl groups, as those terms are defined above, or R' and R" can be taken together to represent an alkanediyl. Non-limiting examples of phosphonate include: Et-P(O)(OMe)(OBn) and C$_5$H$_{11}$—P(O)(OC$_5$H$_{11}$)$_2$. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

In the present specification reference is made to specific isotopes of elements, e.g. gallium-68. Isotopes are designated either with a superscripted mass number prefix or a hyphenated, non-superscripted suffix, e.g. gallium-68 or $^{68}$Ga. Isotopes as disclosed herein should not necessarily be taken to refer to the neutral elements but may refer to ions of these isotopes or to complexes thereof. Thus, for example "$^{68}$Ga" should be taken to refer to a $^{68}$Ga species, e.g. $^{68}$Ga$^{3+}$ or a $^{68}$Ga complex, for example a citrate complex. Such complexes may themselves be neutral or may be electrically charged.

An "excipient" is a pharmaceutically acceptable substance formulated along with the active ingredient(s) of a medication, pharmaceutical composition, formulation, or drug delivery system.

Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle.

Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

An "active ingredient" (AI) or active pharmaceutical ingredient (API) (also referred to as an active compound, active substance, active agent, pharmaceutical agent, radiological agent, imaging agent, biologically active molecule, or a therapeutic compound) is the ingredient in a pharmaceutical drug that is biologically or radiologically active.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "pharmaceutically acceptable carrier," "drug carrier," or simply "carrier" is a pharmaceutically acceptable substance formulated along with the active ingredient that is involved in carrying, delivering and/or transporting a chemical agent. Carriers may be used to improve the delivery and the effectiveness of drugs, including for example, controlled-release technology to modulate drug bioavailability, decrease drug metabolism, and/or reduce drug toxicity. Some carriers may increase the effectiveness of drug delivery to the specific target sites. Some carriers may target specific tissues such as thyroid, brain, gastrointestinal, pancreas, spleen, kidney, neuroendocrine tumors, renal cell carcinoma, lung cancer, breast cancer, prostate cancer, and malignant lymphoma. Non-limiting examples of carriers include: peptides, small molecules, antibodies, or antibody-drug conjugates, or fragments thereof. Further non-limiting examples of carrier molecules include prostate-specific membrane antigen (PSMA), 1,4,7-triazacyclononane-N,N', N"-triacetic acid (NOTA), 1,4,7,10-tetraazacyclododecane-1,4,7,10-tetraacetic acid (DOTA), diethylene triamine pentaacetic acid (DTPA), desferrioxamine, DOTA-Tyr(3)-octreotide (DOTATOC), DOTA-Tyr(3)-Tyr(8)-octreotide (DOTATATE), DOTA-1-naphtyl-alanine (DOTANOC), DOTA-benzothienyl-alanine (DOTA-BOC), DOTA-bombesin, DOTA-arginine-glycine-aspartic acid-bombesin (DOTA-RGD-bombesin), NOTA-RGD, 3,6,9,15-tetraazabicyclo[9.3.1]pentadeca-1(15)-,11,13-triene-3,6,9-triacetic acid-RGD (PCTA-RGD), DOTA-albumin, DOTA-human epidermal growth factor, 1,4,7-triazacyclononane-1-[methyl (2-carboxyethyl)phosphinic acid]-4,7-bis[methyl(2-hydroxymethyl)phosphinic acid-integrin alpha(IIb)beta(3)- specific cyclic hexapeptide (NOPO-RGDfK), 1,4,7-triazacyclononane-1,4-bis(acetic acid)-7-(2-glutaric acid) (NODAGA), NOPO—NaI(3)-octreotide conjugate (NOPO—NOC), 1,4,7-triazacyclononane-1,4,7-tris[(2-carboxyethyl)methylenephosphonic acid] (TRAP(RGD)3), or citrate.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, image, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

III. Production of Gallium-68 to be Purified

In the first step of the method provided herein for preparing a purified, carrier-free $^{68}$Ga solution, a $^{68}$Ga solution comprising $^{68}$Ga to be purified is obtained. The $^{68}$Ga solution comprising $^{68}$Ga to be purified may be prepared through, or a byproduct of, the synthesis of $^{68}$Ga. The $^{68}$Ga to be purified may be synthesized using a cyclotron. A cyclotron is understood to be an apparatus in which charged atomic and subatomic particles are accelerated by an alternating electric field while following an outward spiral or circular path in a magnetic field. Without wishing to be bound by any theory, the $^{68}$Ga to be purified is synthesized via irradiation of a metal sample comprising $^{68}$Zn, which upon irradiation is converted into $^{68}$Ga. The metal sample may be in the form of a liquid target or in the form of a solid target, e.g. a solution of $ZnNO_2$ or solid $^{68}$Zn. When a liquid target is employed, the $^{68}$Zn is dissolved and the liquid target may further comprise an acidic solution. When a solid target is employed, the solid target may be suspended in an acidic solution or an acidic solution may be added upon or after irradiation. The acidic solution may comprise HCl or an acid derived from the dissociation of HCl. Such acids are understood to be the protonated form of a solvent, e.g. $H_3O^+$ in the case of water as a solvent or $CH_3OH_2^+$ in the case of methanol as a solvent. The acid may have a concentration of about 0.1, 0.5, 1, 2, 3, 4, 5, 6, 7, 8, 9, or 10 N. The $^{68}$Ga solution comprising $^{68}$Ga to be purified may be an aqueous solution.

IV. Purification of Gallium-68

In another step, the $^{68}$Ga solution comprising $^{68}$Ga to be purified is contacted with an anion-exchange resin. The anion-exchange resin may be treated with an acidic solution prior to contacting the resin with the $^{68}$Ga solution comprising $^{68}$Ga to be purified. The anion-exchange resin should have a higher affinity for $^{68}$Ga than for zinc, iron, germanium or other impurities so that the impurities are eluted from the anion-exchange resin while the majority, preferably substantially all, of the $^{68}$Ga is retained on the anion-exchange resin under an initial set of conditions. The anion-exchange resin should have an affinity for $^{68}$Ga that can be modulated so as to allow for the $^{68}$Ga to be eluted from the resin under a second set of conditions. The anion-exchange resin may comprise an amine group or phosphonate, e.g. phosphonate, such as the UTEVA® resin. The resin should be resistant to radiation. The methods and systems disclosed herein employ a single anion-exchange resin. Whereas other methods employ a single cation-exchange resin or a combination of two different ion-exchange resins, the methods disclosed herein comprise a single anion-exchange resin. Use of a single anion-exchange resin reduces the amount of time required to purify $^{68}$Ga and provides $^{68}$Ga with a higher specific activity. Commonly, the anion-exchange resins are in particulate form, so that a resin column contains a packed bed of the particulate resin. The resin may be porous, e.g. microporous, mesoporous, nanoporous etc. A typical resin column may contain from about 0.01 g to about 2 g of resin, e.g. about 0.01, 0.05, 0.1, 0.15, 0.2, 0.3, 0.4, 0.5, 1, 1.5, or 2 g.

After contacting the anion-exchange resin with the $^{68}$Ga solution comprising $^{68}$Ga to be purified, the resin may be optionally washed with a washing solution. The washing solution may comprise an acid, including but not limited to HCl, or an acid derived from the dissociation of the acid, e.g. $H_3O^+$. The acid of the washing solution may have a concentration of greater than 1 N, such as from about 2 N to 8 N, e.g. 2 N, 3 N, 4 N, 5 N, 6 N, 7 N, or 8 N. The washing solution may be an aqueous solution.

Following the optional washing step, $^{68}$Ga is eluted from the anion-exchange resin by contacting the anion-exchange resin with an eluting solution. Without wishing to be bound by theory, the eluting solution modulates the affinity of the anion-exchange resin for $^{68}$Ga. The eluting solution may comprise an acid, including but not limited to HCl, or an acid derived from the dissociation of the acid, e.g. $H_3O^+$. The acid of the eluting solution may have a concentration of from about 0.005 N to about 2 N, e.g. 0.005 N, 0.01 N, 0.02 N, 0.03 N, 0.04 N, 0.05 N, 0.06 N, 0.07 N, 0.08 N, 0.09 N, 0.1 M, 0.5 N, 1 N. or 2 N. The eluting solution may be an aqueous solution.

The resulting purified, carrier-free $^{68}$Ga solution has a specific activity of greater than about 25 GBq/μg. The specific activity may be from about 25 GBq/μg to about 100,000 GBq/μg e.g. 25, 100, 500, 1000, 10,000, 15,000, 20,000, 25,000, 30,000, 31,000, 32,000, 33,000, 33,100, 33,200, 33,300, 33,400, 33,500, 33,600, 33,700, 33,800, 33,900, 34,000, 35,000, 36,000, 37,000, 38,000, 39,000, 40,000, 50,000, 60,000, 70,000, 80,000, 90,000, or 100,000 GBq/μg. Specific activity values present in this disclosure are correlated to the End of Bombardment (EOB) unless explicitly noted otherwise.

The present disclosure also provides systems for preparing a purified, carrier-free $^{68}$Ga solution. These systems comprise a solid target comprising $^{68}$Zn, a cyclotron, wherein the solid target is irradiated using the cyclotron, and a single anion-exchange resin. The system may be portable or may be fixed in a specific location.

V. Compositions of Gallium-68 for Imaging

The present disclosure also provides compositions comprising the purified, carrier-free solution of $^{68}$Ga. Compositions may further comprise a carrier molecule. The compositions disclosed herein may be useful for biological imaging, e.g. PET imaging. Compositions may be prepared by the addition of the purified, carrier-free solution of $^{68}$Ga to a carrier molecule or a solution comprising a carrier molecule. Further processing of the composition may be performed prior to administration to a patient. Such processing may include purification, concentration, or dilution. Compositions of the present disclosure may also comprise pharmaceutically acceptable excipients.

The compositions disclosed herein may be formulated for administration intraarterially, intraarticularly, intracranially, intrapericardially, intraperitoneally, intratumorally, intravenously, intravesicularlly, parenterally, via injection, via local delivery, or via localized perfusion. The compositions may be administered once or more than once. The compositions may be used to image tissue, such as a tumor, e.g. a prostate, pancreatic, lung, or neuroendocrine tumor. The compositions may be used to image a tumor that exhibits elevated levels of PSMA.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis, Purification, and Analysis of $^{68}$Ga

All reagents and solvents were purchased from commercial vendors and used directly unless otherwise noted. Enriched $^{68}$Zn metal powder (99+% purity) was purchased from ISOFLEX USA (San Francisco, Calif.). Milli-Q water (18 MΩ·cm) was obtained from a Millipore Milli-Q Integral 5 water purification system (Billerica, Mass.). The ITG $^{68}$Ge/$^{68}$Ga Generator (GMP) was obtained from RadioMedix (Houston, Tex.). UTEVA® resin (50-100 μm) was purchased from Eichrom (Lisle, Ill.). Hydrochloric acid (33% min., 99.999999% metal basis) was obtained from Alfa Aesar (Pittsburgh, Pa.) and was diluted to 10 N, 4 N, and 0.05 N with Milli-Q water. 1,4,7,10-Tetraazacyclododecane-1,4,7,10-tetraacetic acid (DOTA) was purchased from Sigma-Aldrich (St. Louis, Mo.). Instant thin-layer chromatography paper (iTLC-SG) was acquired from Fisher Scientific (Hampton, N.H.). The labeling efficiency of $^{68}$Ga-DOTA was determined using radio-TLC with the mobile phase composed of 10% ammonium acetate and methanol in one-to-one ratio. The radio-TLC plates were scanned using a Bioscan AR-2000 radio-TLC scanner (Washington, D.C.).

The Cyclotron Radiochemistry Facility (CRF) is equipped with a 16.5 MeV proton energy cyclotron (PETrace, GE Healthcare, Waukesha, Wis.). Prior to irradiation, a 7 mm diameter of enriched $^{68}$Zn (60-120 mg) was electrodeposited on a platinum disc using a solution comprised of $^{68}$ZnCl$_2$ and 0.05 N HCl (concentration of $^{68}$Zn: 25-30 mg/mL) and a current density of 25 mA/cm$^2$. The target was then transferred and mounted in the PETtrace cyclotron through the Comecer EDS/PTS module (Castel Bolognese RA, Italy). The target was irradiated at an incident proton-beam energy of 14.5 MeV with beam currents of 15-40 pA. After irradiation, the target was pneumatically retrieved. Chemical separation of $^{68}$Ga was performed and labeling procedures were conducted using the Comecer EDS and GE Healthcare TRACERlab FX modules.

Gallium-68 was separated from $^{68}$Zn using a column containing 100 mg of UTEVA® resin, in which the resin was pre-conditioned with 10 mL of 6 N HCl. Upon retrieving the irradiated $^{68}$Zn target from the cyclotron into the Comecer EDS module, the target was completely dissolved with 10 mL of 6 N HCl under 10 min. The crude $^{68}$Ga/$^{68}$Zn solution was passed through the column containing the UTEVA® resin. After rinsing the transfer lines in the EDS module with 5 mL of 6 N HCl, the HCl rinse was also passed through the column followed by 40 mL of 4 N HCl to remove residual $^{68}$Zn and any additional metal contaminants. The [$^{68}$Ga]GaCl$_3$ was desorbed from the resin with 2 mL of 0.05 N HCl and readily available to be used in a labeling reaction without any further processing.

The effective specific activity (GBq/μmol) of [$^{68}$Ga]GaC$_3$ was determined through a series of labeling reactions with a chelating solution. Since DOTA is one of the chelators that is often conjugated to a biomolecule for labeling with $^{68}$Ga, multiple dilutions of DOTA solution (2.48×10$^{-5}$-2.48×10$^2$ μM) in 0.5 M acetate buffer (pH 4.5) were used for the study. A volume of 5 μL (~74 MBq) of [$^{68}$Ga]GaCh$_3$ was first diluted with 1 mL of 0.05 M HCl as a stock solution. The study was performed by adding 50 μL of [$^{68}$Ga]GaCl$_3$ stock solution into 200 μL of DOTA solution. The reactions were allowed to precede at 95° C. for 20 min. After incubation was completed, the effective specific activity was determined by measuring labeling efficiency using radio-TLC analysis (mobile phase: 10% ammonium acetate/methanol, 1:1 (v/v)).

Samples containing activities of 0.5-1.0 μCi (18.5-37 KBq) of [$^{68}$Ga]GaCl$_3$ in 2 mL microcentrifuge tubes were diluted with Milli-Q water to bring the final volume to 1 mL. The radionuclidic purity was then determined by gamma-my spectroscopy using a cryogenically cooled germanium (HPGe) detector (ORTEC, Oak Ridge, Tenn.). Samples were counted for 1 h starting immediately after End of Synthesis (EOS) and the measurement was repeated after 24 h. The radionuclidic purity of $^{68}$Ga was based on the analysis of the regions of interest (ROI) at EOS and of decayed samples.

ICP-MS analysis of the $^{68}$Ga samples, after decay, were conducted at the University of Missouri Research Reactor (MURR). All samples were analyzed on a PerkinElmer NexION 300x ICP-MS operated in kinetic energy discrimination (KED) mode with two different helium cell gas flows at 2.5 and 4.5 mL/min. The amount of gallium, germanium, iron, and zinc in each sample were determined.

Example 2: Evaluation of Cyclotron Irradiated $^{68}$Zn Targets and $^{68}$Ga Separation and ICP-MS Analysis Due to the unique characteristics and availability of $^{68}$Ge/$^{68}$Ga generators, several efforts have been made to translate $^{68}$Ga-labeled compounds from preclinical evaluations into routine clinical practice (Amor-Coarasa et al., 2016; Velikyan, 2015; Vis et al., 2015). In order to satisfy the increasing demand for $^{68}$Ga in preclinical and clinical applications, an approach to reliably produce $^{68}$Ga via $^{68}$Zn(p,n)$^{68}$Ga reaction in significantly large quantities was investigated. The methods described herein have been used successfully for the cyclotron production and chemical separation of $^{68}$Ga. See Table 1 for a comparison of $^{68}$Ga production at various facilities.

TABLE 1

Comparison of $^{68}$Ga Production at Various Facilities

| z | MDACC[1] | Mayo Clinic/GE[2] | University of Coimbra/IBA[3] |
|---|---|---|---|
| Target forms | Solid | Liquid | Liquid |
| Amount of $^{68}$Zn | 80 mg | 200 mg | 200 mg |
| Beam energy | 14.5 MeV | 14 MeV | 14.2 MeV |
| Production yield at EOB | 2.72 ± 0.08 GBq/µg · h | 0.9 ± 0.01 GBq/µg · h | 0.3 GBq/µg · h |
| Optimized $^{68}$Ga processing | Yes (1 column processing) | No | Yes (3 column processing) |

[1]Lin et al., 2018; [2]Pandey et al., 2014; [3]Alvesa et al., 2017.

Due to the relatively low melting point of Zn metal (419.5° C.), initial tests with natZn targets were conducted for short time intervals (5 min) at an incident proton-beam energy of 14.5 MeV while increasing beam currents from 15 to 40 pA. No significant heat effects on the electrodeposited natZn were observed throughout the tests indicating efficient heat removal from the target by the EDS/PTS module cooling system. To ensure production reliability during long irradiations targets were tested with beam currents up to 40 pA. No visible heat effects or loss of yield was observed. All subsequent measurements reported here were conducted at a beam current of 30 pA. To optimize target thickness for maximum yield, targets with a diameter of 7 mm and a mass of $^{68}$Zn between 60 and 120 mg were bombarded for 20-90 min. The $^{68}$Ga activity at End of Bombardment (EOB) correlated well with irradiation time and amount of $^{68}$Zn metal present. Targets containing (104.1±2.7) mg $^{68}$Zn (n=3) irradiated for 1 h at a beam current of 30 µA resulted in 60.9±1.8 GBq (1645±51 mCi) of $^{68}$Ga at EOB. The production yield was found to be 2.72±0.08 GBq/pA·h (73.5±2.3 mCi/pA·h). Sadeghi et al. reported production of $^{68}$Ga using a 6° grazing incidence target geometry with a proton-beam energy of 15.0 MeV and a beam current of 150 µA (Sadeghi et al., 2009). They report a production yield for a target mass of 434 mg of 5.03 GBq/µA·h (136 mCi/µA·h) at EOB for a short 15 min irradiation. Their result is not far from the calculated value of 5.81 GBq/µA·h (157 mCi/µA·h) presented by Szelecsényi et al. derived from cross section measurements (Szelecsényi et al., 2012). These results compare well with these reported values taking into account the lower incident proton-energy employed herein to minimize $^{67}$Ga impurities and a reduced target density of (4.8±0.4) g/cm$^3$ based on target thickness measurements.

During initial development the time required to dissolve the irradiated $^{68}$Zn target was investigated. The target was dissolved using 10 mL of 10 N HCl. The completion of the dissolution process was monitored using the flow meter integrated into the system. At the beginning of the dissolution process hydrogen gas was released partially interrupting the overall flow rate of circulating HCl solution. Once the target was completely dissolved and no more hydrogen gas was being released, the flow rate was re-stabilized. Based on these observations (and posterior verification) we found the total dissolution time required was less than 5 min. High zinc and HCl acid contents in the final $^{68}$Ga solution are two potential challenges for cyclotron-produced $^{68}$Ga. Although previous reports indicate that most $^{68}$Zn can be removed by using the AG® 50W cation resin alone (Engle et al., 2012; Pandey et al., 2014), lower specific activity is obtained as it takes a relatively long time (i.e., usually more than an hour) to evaporate the $^{68}$Ga solution and reconstitute it with a low concentration of HCl for radiolabeling use. McAlister and Horwitz have established a two-column system which utilizes AG® 50W cation resin and UTEVA® anion resin to minimize $^{68}$Ge breakthrough from a $^{68}$Ge/$^{68}$Ga generator (McAlister and Philip Horwitz, 2009). However, the two-column system again results in lower specific activity due to processing times. By adapting this concept for processing $^{68}$Ga from an irradiated $^{68}$Zn target, over 75% of $^{68}$Ga produced activity (decay corrected) can be recovered while the cyclotron-produced $^{68}$Ga solution results in lower (p<0.01) zinc content (0.004±0.002 µg/GBq) when compared to that of generator-produced $^{68}$Ga (0.37±0.09 µg/GBq) after ICP-MS analysis. In addition, low iron content was observed in both cyclotron and generator-produced $^{68}$Ga. The germanium was below detection limits for cyclotron-produced $^{68}$Ga (See Table 2). It was found that the UTEVA® anion-exchange resin could be used to generate $^{68}$Ga solutions with high purity and very high specific activity without the need for additional processing. All of these data suggest that the method presented herein not only minimizes zinc and other metal impurities, but also allows the reconstitution of the final $^{68}$Ga solution in a low concentration of HCl as well. The whole separation process only takes less than 10 min, which is especially important for $^{68}$Ga production.

TABLE 2

Comparison of Generator- vs. Cyclotron-Produced $^{68}$Ga

| | Generator-produced $^{68}$Ga$^a$ | Cyclotron-produced $^{68}$Ga$^b$ |
|---|---|---|
| Effective Specific Activity (GBq/µmol) | 7.06 ± 1.61 | 6.74 ± 0.83 |
| Absolute Specific Activity (GBq/µg)$^c$ | ~2,500 | ~25,000$^d$ |
| Zn residue (µg/GBq) | 0.37 ± 009 | 0.004 ± 0.002 |
| Fe residue (µg/GBq) | 0.12 ± 0.03 | 0.11 ± 007 |
| Ge residue (µg/GBq) | 0.0013 ± 0.0001 | Less than 0.0001 |
| Isotope Impurities | $^{68}$Ge ($T_{1/2}$: 271 d), less than 0.005% | $^{67}$Ga ($T_{1/2}$: 3.3 d), less than 0.3% |
| Activity Acquired | Up to 40-45 mCi/elution | ~1.0 Ci at EOB with 1 h irradiation |

TABLE 2-continued

Comparison of Generator- vs. Cyclotron-Produced $^{68}$Ga

|  | Generator-produced $^{68}$Ga[a] | Cyclotron-produced $^{68}$Ga[b] |
|---|---|---|
| $^{68}$Ga Processing Time After Irradiation | N/A | Less than 30 min |
| Cost | 60,000 USD/12 month | Less than 200 USD/batch without $^{68}$Zn recovery |

[a]Generator-produced $^{68}$Ga was purified via two-column method, employing AG® 50W and UTEVA® columns;
[b]Cyclotron-produced $^{68}$Ga was purified with a single UTEVA® column.
[c]Correlated to End of Synthesis.
[d]Value correlated to End of Bombardment is ~33,500 GBq/μg.

The effective specific activity of cyclotron and generator-produced $^{68}$Ga was determined by DOTA titration using radio-TLC. While the $^{68}$Ga-DOTA radio-peak migrates to the solvent front, the unreacted [$^{68}$Ga]GaCl$_3$ remains at the origin. In all experiments (n=3 for each study), the effective specific activity of cyclotron and generator-produced [$^{68}$Ga] GaCl$_3$ was found to be 6.7±0.8 and 7.1±1.6 GBq/μmol, respectively. No statistically significant difference (p=0.775) was found in the effective specific activity between cyclotron and generator-produced $^{68}$Ga. To confirm the radionuclidic purity of the $^{68}$Ga solution produced via the $^{68}$Zn(p, n)$^{68}$Ga reaction, gamma-ray spectroscopy was performed. A small fraction (≤0.2%) of 6~Ga was observed when the target was irradiated up to 90 min with 14.5 MeV protons.

All of the compounds, systems, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.

Alvesa et al., *Mod. Phys. Lett. A*, 32:1740013, 2017.
Ambrosini and Fanti, "$^{68}$Ga-DOTA-peptides in the diagnosis of NET," *PET Clin.* 9:37-42,2014.
Amor-Coarasa et al., "Comprehensive quality control of the ITG 68Ge/$^{68}$Ga generator and synthesis of $^{68}$Ga-DOTA-TOC and $^{68}$Ga-PSMA-HBED-CC for clinical imaging,".*J Nucl. Med.*, 57:1402-1405, 2016.
Anderson, *Practical Process Research & Development A Guide for Organic Chemists*, 2$^{nd}$ ed., Academic Press, New York, 2012.
Belosi et al., "Generator breakthrough and radionuclidic purification in automated synthesis of $^{68}$Ga-DOTANOC," *Curr. Radiopharm.* 6:72-77, 2013.
Engle et al., "Very high specific activity —$^{68}$Ga from zinc targets for PET," *Appl. Radiat. Isotopes*, 70:1792-1796, 2012.
*Handbook of Pharmaceutical Salts: Properties, and Use*, Stahl and Wermuth Eds., Verlag Helvetica Chimica Acta, 2002.
Jensen and Clark, "Direct production of Ga-68 from proton bombardment of concentrated aqueous solutions of [Zn-68] zinc chloride," In: *Proceedings of the 13$^{th}$ International Workshop on Targetry and Target Chemistry Proceedings*, pp. 288-292, 2011.
Lin et al., *Appl. Radiat. Isot.*, 133: 1-3, 2018.
Lindenberg et al., "Prostate cancer imaging with novel PET tracers." *Curr. Urol. Rep.*, 17:18, 2016.
McAlister et al., "Automated two column generator systems for medical radionuclides," *Appl. Radiat. Isotopes*, 67:1985-1991, 2009.
Pandey et al., "Cyclotron production of $^{68}$Ga via the $^{68}$Zn (p,n)$^{68}$Ga reaction in aqueous solution," *Am. J. Nucl. Med.* Mo. Imaging, 4:303-310, 2014.
Prata. "Gallium-68: a new trend in PET radiopharmacy," *Curr. Radiopharm.* 5:142-149, 2012.
Reagan-Shaw et al. *FASEB J.* 22(3):659-661, 2008.
Sadeghi et al., "Cyclotron production of $^{68}$Ga via proton-induced reaction on $^{68}$Zn target," *NUKLEONIKA*, 54:25-28, 2009.
Schwenck et al., "Comparison of $^{68}$Ga-labelled PSMA-11 and $^{11}$C-choline in the detection of prostate cancer metastases by PET/CT," *Eur. J. Nucl. Med.* Mol. Imaging, 44:92-101, 2017.
Shamim et al., "PET/Computed tomography in neuroendocrine tumor: value to patient management and survival outcomes. *PET Clin.* 10, 411-421, 2015.
Siikanen, "Cyclotron produced Ga-66/68 with thermal diffusion-assisted bulk separation and AG50W-X8/UTEVA purification," *Radiometals* 2013 in Sonoma Valley, 7, Jun. 13-16, 2013.
Smith, *March's Advanced Organic Chemistry: Reactions. Mechanisms. and Structure.* 7$^{th}$ Ed. Wiley. 2013.
Szelecsényi et al., "Investigation of direct production of $^{68}$Ga with low energy multiparticle accelerator," *Radiochim. Acta*, 100:5-11, 2012.
Tolmachev and Lundqvist, "Rapid separation of gallium from zinc targets by thermal diffusion," *Appl. Radiat. Isot.: Tech. Note*, 47:297-299, 1996.
Velikyan, "$^{68}$Ga-Based radiopharmaceuticals: production and application relationship," *Molecules*, 20:12913-12943, 2015.
Virgolini et al., "Current knowledge on the sensitivity of the (68)Ga-somatostatin receptor positron emission tomography and the SUVmax reference range for management of pancreatic neuroendocrine tumours," *Eur. J. Nucl. Med. Mol. Imaging* 43:2072-2083, 2016.
Vis et al., "GMP-compliant $^{68}$Ga radiolabelling in a conventional small-scale radiopharmacy: a feasible approach for routine clinical use" *EJNMMI* Res., 5:27, 2015.

What is claimed is:

1. A method of preparing a purified, carrier-free $^{68}$Ga solution comprising:
   a) obtaining a $^{68}$Ga solution to be purified comprising $^{68}$Ga;
   b) contacting the $^{68}$Ga solution with an anion-exchange resin, wherein the anion-exchange resin comprises a phosphonate or a substituted phosphonate; and
   c) eluting the $^{68}$Ga from the anion-exchange resin to obtain the purified, carrier-free $^{68}$Ga solution.

2. The method of claim 1, wherein the method comprises contacting the $^{68}$Ga solution to be purified with a single anion-exchange resin.

3. The method of claim 1, wherein the method does not comprise contacting the $^{68}$Ga solution to be purified or the purified, carrier-free $^{68}$Ga solution with another ion-exchange resin.

4. The method of claim 1, wherein the $^{68}$Ga in the $^{68}$Ga solution to be purified is prepared by synthesizing the $^{68}$Ga in the $^{68}$Ga solution.

5. The method of claim 4, wherein a cyclotron is used to synthesize the $^{68}$Ga.

6. The method of claim 5, wherein the cyclotron comprises a metal sample in the form of a liquid target.

7. The method of claim 6, wherein the metal sample comprises $^{68}$Zn$^{2+}$.

8. The method of claim 5, wherein the cyclotron comprises a metal sample in the form of a solid target.

9. The method of claim 8, wherein the metal sample comprises $^{68}$Zn.

10. The method of claim 1, wherein the $^{68}$Ga solution to be purified comprises an acid.

11. The method of claim 1, wherein the $^{68}$Ga solution to be purified is an aqueous solution.

12. The method of claim 1, wherein the anion-exchange resin comprises a phosphonate.

13. The method of claim 12, wherein the anion-exchange resin comprises dipentyl pentylphosphonate.

14. The method of claim 1, wherein the method further comprises washing the anion-exchange resin with a washing solution.

15. The method of claim 1, wherein the purified, carrier-free $^{68}$Ga solution has an activity of from about 37 MBq to about 370 GBq.

\* \* \* \* \*